United States Patent [19]

Blank et al.

[11] 4,248,855
[45] Feb. 3, 1981

[54] PHARMACEUTICAL BASE SALTS

[75] Inventors: Izhak Blank; Joseph Fertig, both of Haifa, Israel

[73] Assignee: Hydrophilics International, Inc., New York, N.Y.

[21] Appl. No.: 718,126

[22] Filed: Aug. 27, 1976

Related U.S. Application Data

[63] Continuation-in-part of Ser. No. 614,951, Sep. 19, 1975, abandoned.

[51] Int. Cl.³ ............................................. A61K 31/78
[52] U.S. Cl. ........................................ 424/19; 424/78; 424/80; 424/81
[58] Field of Search .......................... 424/19–22, 424/78–81

[56] References Cited

U.S. PATENT DOCUMENTS

| | | | |
|---|---|---|---|
| 3,450,814 | 6/1969 | Bechtold | 424/180 |
| 3,608,063 | 9/1971 | Banker | 424/22 |
| 3,629,392 | 12/1971 | Banker et al. | 424/22 |
| 3,845,201 | 10/1974 | Haddad et al. | 424/22 |
| 3,870,791 | 3/1975 | Haddad et al. | 424/22 |
| 3,935,303 | 1/1976 | Khromov et al. | 424/14 |
| 3,978,201 | 8/1976 | Khromov et al. | 424/7 |

*Primary Examiner*—Shep K. Rose
*Attorney, Agent, or Firm*—Schuyler, Banner, Birch, McKie & Beckett

[57] ABSTRACT

A salt of a polymer, containing acid groups, soluble or dispersible in water or organic solvents, is combined with a salt-forming pharmaceutically effective compound for application, orally, topically, or systemically. A sustained release of the pharmaceutical compound is thus obtained.

16 Claims, No Drawings

PHARMACEUTICAL BASE SALTS

RELATIONSHIP TO COPENDING APPLICATIONS

This application is a continuation-in-part of appliation Ser. No. 614,951, filed Sept. 19, 1975 in the names of Izhak Blank and Joseph Fertig, entitled "Agricultural Compositions & Methods," now abandoned. This application is based upon and also claims the benefit of the filing dates of British applications Ser. Nos. 35295/75, filed Aug. 27, 1975; 35296/75, filed Aug. 27, 1975; 23962/76, filed June 10, 1976; and 23963/76, filed June 10, 1976.

A problem that exists with the application of many compounds having pharmaceutical (including veterinary) activity is that they do not remain sufficiently long in the location where it is required for them to exert their effect. Compounds that are to act internally can, of course, be formulated in various slow release compositions, for example being encapsulated within polymers that dissolve only slowly in the intestine or stomach, but such slow release compositions cannot be used for many pharmaceutical applications, especially topical applications.

Many pharmaceutically active compounds are basic compounds and are capable of forming salts. Many such compounds are generally used in the form of a salt, generally with a simple mineral acid such as hydrochloric or nitric acid. This is because the salt form is generally more stable than the basic form. The salt is also more water soluble. For some purposes this may be convenient, but it does have the serious disadvantage of ensuring fairly quick removal of the compound from the location where the compound is required to exert its effect. As one example of this problem, pilocarpine is a useful medicament for the treatment of eye disorders and the conventional way of administering it is to apply a solution or ointment of pilocarpine nitrate but this is quickly rinsed from the eye surface by the tear fluid. In U.S. Pat. No. 3,630,200 a drug dispensing ocular insert is described consisting of an inner core containing the drug surrounded by an outer layer of hydrophilic material through which the pilocarpine slowly diffuses into the eye. However there are various problems incurred with the use of such an insert. For instance there is always the risk of the insert rupturing so as to release suddenly a very high level of the medicament.

As another example with most medicaments, for example anaesthetics and analgesics and various others, there is a minimum concentration level below which the material does not produce the required effect and a maximum concentration level above which toxic side effects begin to be noticed, and it is desirable to keep the concentration of the medicament as close as possible to the minimum effective level. Normally when these medicaments are applied in conventional carries if they are applied to a location at near the minimum effective level their concentration drops rapidly such that very soon after application the medicament does not exert the desired effect. To prolong action it is therefore normal to apply the medicament considerably above the minimum effective level, but this increases the risk of toxic side effects.

Accordingly it has been our object to devise some means of applying a salt-forming pharmaceutically effective compound to a human or animal body at a rate that is more uniform and/or for a duration that is longer than when the compound is applied in conventional manner, e.g. as a nitrate or hydrochloride salt.

According to the invention there is provided a salt of a polymer containing acid groups that is soluble or dispersible in water or common organic solvents with a salt forming pharmaceutically effective compound.

By saying that the polymer is soluble or dispersible in water or common organic solvents we mean that it is capable of being dissolved or emulsified as a liquid phase in water or a common organic solvent. The preferred common organic solvents are, as is well known, aliphatic compounds such as lower alkanols, e.g. containing 1 to 4 carbon atoms (such as methyl, ethyl or isopropyl alcohol), lower ketones, e.g. containing 1 to 6 carbon atoms (e.g. acetone or methyl ethyl ketone) dimethyl formamide, halogenated lower hydrocarbons containing 1 to 4 carbon atoms, e.g. chloroform, mixtures thereof and mixtures of one or more of these with water.

As a result of using a polymer that is soluble or dispersible in water or a common organic solvent it is possible to form the salt by an entirely liquid phase reaction, and this is preferred. Thus the polymer in the form of a solution or emulsion is mixed with the pharmaceutically effective compound to form a salt, which normally also is soluble or dispersible in water or common organic solvents. In fact it is preferred that the salt should be water soluble or water swellable, that is to say that over a period of hours or days the salt dissolves in water or swells substantially, e.g. to form a gel.

However the salt of a phramaceutical base with the polymeric acidic compound will obviously be much less soluble and diffusible through body membranes than a salt with a simple monomeric acid such as hydrochloric acid.

The polymer may be a homopolymer of a monomer containing an acid group, and which is thus generally hydrophilic, or it may be a copolymer of different monomers, some or all of which contain acid groups. The monomers are preferably vinyl monomers. Usually more than 10%, preferably more than 25% and most preferably more than 40% by weight of the monomers from which the polymer is made contain an acid group.

In general it is preferred to use 10–100%, most preferably 25–100%, by weight, of hydrophilic monomers, and 0–90%, most preferably 0–75%, by weight, hydrophobic monomers.

Naturally the particular choice of monomers will be made having regard to the desired solubility or dispersability of the polymer and the desired water resistance, slow release and other properties required of the salt in the particular formulation in which it is to be applied. In addition to controlling these properties by appropriate choice of the balance between hydrophilic and hydrophobic monomers, they can also be controlled by cross-linking, for instance by including a small amount of a trifunctional cross-linkable monomer in the monomer mixture from which the polymer is made. The amount of cross-linkable monomer is generally small, for instance 1–15% by weight, preferably 1–10% by weight. Preferred polymers for use in the invention are free of cross-linking agent and comprise both hydrophilic monomers and hydrophobic monomers. Preferably they comprise from 10 to 75%, and most preferably 10 to 55% hydrophilic monomers and 20 to 80%, most preferably 30 to 60%, hydrophobic monomers.

Suitable hydrophilic monomers include monomeric acids, such as acrylic, methacrylic, itaconic, crotonic, vinyl sulfonic, maleic, angelic, oleic, or α-chloro-acrylic acid or sulfoethyl-methacrylate and vinyl pyrrolidone. Any of these, except vinyl pyrrolidone, may be used as the sole hydrophilic monomer or two or more may be used together. Naturally dicarboxylic acids such as maleic acid may be introduced in the form of the anhydride.

Suitable hydrophobic monomers include alkyl acrylates, alkyl methacrylates, vinyl ethers, acrylonitrile, hydroxymethacrylate, styrene and vinyl acetate. The alkyl groups in alkylacrylates and alkylmethacrylates usually contain 1 to 4 carbon atoms, e.g. ethyl, methyl or butyl, but longer chain groups containing up to, say, 18 carbon atoms, e.g. lauryl, can be used. In particular when hydrophobic monomer is present, part at least of it can be a plasticising monomer in a proportion of 5% to 20% by weight, preferably about 10%. Suitable plasticising monomers are long chain esters of acrylic or methacrylic acid, e.g. ethyl hexyl acrylate.

Particularly preferred polymers are copolymers of hydrophilic groups selected from acrylic acid, vinyl pyrrolidone, methacrylic acid and maleic anhydride and hydrophobic monomers selected from methyl methacrylate, butyl methacrylate, lauryl methacrylate, methylacrylate, 2-ethyl-hexylacrylate and styrene. Most preferably the polymer includes acrylic acid with or without vinyl pyrrolidone. Particularly preferred are polymers containing from 20 to 55% acrylic acid.

By appropriate choice of the monomers and their proportions it is easily possible to formulate, with any particular pharmaceutically active basic compound, a series of salts ranging from completely water soluble to completely water insoluble. It is also possible to design the polymer so that self-emulsifying compositions are obtained. This is done by partially neutralising the polymer with the drug base and further neutralising with an organic or inorganic base such as ammonia or sodium hydroxide, which, in fact, converts the polymer into an emulsifier.

The polymerisation of the monomers can be made by the usual technique, either in bulk, solution, emulsion or dispersion polymerisation, using catalysts such as those well known in the art. Preferably they are made by emulsion or solution polymerisation.

Other materials which can be included before or after the polymerisation include plasticisers, emulsifiers, stabilisers and humectants.

The salts of the invention are best made merely by mixing the salt forming pharmaceutically effective compound with the polymer while the polymer is in a liquid phase, either as the liquid phase in an emulsion or as a solution. The amount of pharmaceutical base may be stoichiometric, so that substantially all the acid groups are neutralised by the pharmaceutically effective base, but often less than the stoichiometric amount is used, so that the resultant salt contains an excess of acid groups. The excess may be, for instance, at least 20%, preferably at least 50%. These excess acid groups may be neutralised at least partially as mentioned above or left free.

A wide variety of salt forming pharmaceutically effective compounds may be used in the invention. Preferred are salt forming local anaesthetics, since these generally have a hydrophilic amino group connected by an intermediate group to lipophylic aromatic residue, and salt forming analgesic materials, which also generally contain an amino group. In the prior art such materials have generally been formulated as the hydrochloride, sulphate, borate, tartrate, hydrobromide, citrate, lactate or benzoate or similar salt of an inorganic or organic acid, the active part of the molecule being the free base which is created in situ by the hydrolysis of the salt. Typical anaesthetics that can be used in the invention include Procaine, Benoxinate, Butethamine, Chloroprocaine, Cocaine, Cyclomethylcaine, Dibucaine, Dimethisocaine, Hexylcaine, Lidocaine, Mepivacaine, Naepaine, Phenacaine, Piperocaine, Pramoxine, Prilocaine, Proparacaine, Tetracaine and any other member of this class of compounds. Typical analgesics that can be used in the invention include opium, alkaloids, namely morphine, codeine, heroin, the antagonist nalorphine, and synthetic analgesics such as Meperidine, Methadone, Levophan, Phenazocine, Propoxyphene, Ethoheptazine and Pentazocine. The anaesthetic and analgesic materials can be used in accordance with the formulations of this invention either singly or in combinations containing two or more of the active materials. It is also possible to further change the duration of activity of the drugs by using them in combinations with a vasoconstrictor, such as Ephinephrine, Ephedrin, or similar drugs which also give polymer salts under the conditions of this application.

It will be observed that many of these compounds are alkaloids and in general it is preferred that the pharmaceutically effective compound should be an alkaloid. A particularly preferred alkaloid is pilocarpine, which is useful for the treatment of eye disorders.

Typical other alkaloids and other compounds that can be used in the invention as the salt forming pharmaceutically effective compound include Reserpine, Ephedrine, Colchisean, Caffein, Atropine, Scopalamine, Benzocaine, Dibucaine, Epinophrein, the amphetamines, Phenoxybenzamine, Histamine, Batazol, Diphenylhydramines, Pyrilamine, Cyclizine, Phenothiazines such as Chlorpromazine and Methadone, and Clordiazoepoxides such as "Librium". Also sulphonamides, such as Sulphadimetoxin, can be used.

In general any compound having pharmaceutical (including veterinary) activity and having a basic site capable of forming a salt with a polymeric acid can be used in the invention.

The composition can be in the form of a solid, for instance, being a film that is preformed before application to the human or animal body, or other shaped solid, for instance an ocular eye insert or a surgical implant that can be implanted in some particular position in the body so as to give slow release in that position only. Such a composition will generally consist solely of the polymer salt. Other compositions include conventional pharmaceutical, including veterinary, formulations such as powders or other solid compositions and oils or creans or other liquid compositions. Powdered compositions will comprise the polymer salt in powder form, optionally together with a carrier, such as talc. Creams, oils and other liquid compositions will comprise a solution or emulsion of the polymer salt optionally with conventional carriers for liquid compositions. The compositions may be formulated for oral, topical or systemic application, preferably topical.

By having the pharmaceutically effective compound chemically combined with the polymer a stable form of compound is produced, since such compounds are generally more stable that the free base, and the invention permits wide control of the rate of hydrolysis of the salt. Thus it can be regulated by varying the characteristics of the polymer, such as the ratio between its hydrophilic and hydrophobic components and their nature and molecular weight and also by varying the physical form of the product, i.e. by formulating it as a solution, suspension, emulsion, film or other shaped body, suppository or ointment, and thus it is possible to obtain a much better control of the rate of release, especially in topical applications, than has generally been possible previously.

The invention is of particular value when applied to the treatment of eye disorders using pilocarpine. Thus according to the invention an ocular insert may be formed of a salt of pilocarpine with a polymer containing acid groups, as described above. Preferably the polymer and the salt are so formulated that the salt slowly absorbs water over a period of many hours and swells to a gel. This gives enough time for the drug to be absorbed by the eye tissues whilst the polymeric part is carried away from the ocular and nasal canals. Alternatively the salt and polymer can be so formulated that although the insert swells and is sufficiently hydrophilic to release pilocarpine into the eye the insert itself does not entirely disappear and instead has to be removed after the desired period of treatment.

Such inserts can be made by, for example, casting a solution of the desired salt.

Another particularly valuable composition of the invention, of especial use for the treatment of glaucoma, is an emulsion of a pilocarpine salt of a polymer containing acid groups, which can then be used as eye drops. It is noteworthy that in a recent publication (M. C. Makoid et al, J. Pharm. Sci. 65, 150, 1976), it is indicated that corneal uptake from pilocarpine nitrate is much lower than thought heretofore, the fraction of that absorbed being 0.002 to 0.003 only. Most of the drug is lost in the pre-corneal area. By using the form of medication described in the present application, the contact time is much prolonged, the loss in the pre-corneal area is reduced, and the general efficacy and duration of effect are considerably improved.

A particular advantage of pilocarpine-polymer emulsions, and indeed of all pharmaceutical compositions of the invention, is that it is possible to formulate a composition containing a higher content of pharmaceutically effective compound than is customarily possible with the same compounds. For instance pilocarpine hydrochloride opthalmic solution generally contains 0.5 to 10% salt while pilocarpine nitrate opthalmic solution generally contains from 2 to 6% of the salt and pilocarpine eye drops generally contain up to 5%. In practice very few pilocarpine compositions contain more than 6% pilocarpine. As is shown by the examples below very satisfactory results can be obtained in the invention using compositions containing more than 10% and usually more than 12% of the active ingredient. Thus very satisfactory emulsions containing 12% pilocarpine base (equivalent to 14.1% hydrochloride and 15.6% nitrate) can be formulated and used very satisfactorily and it is easily possible to formulate compositions containing greater amounts of pilocarpine or other pharmaceutically active compound.

Some Examples are now given. In these all percentages are by weight unless otherwise stated.

A series of polymers were prepared by conventional solution or emulsions polymerisation of vinyl monomers using conventional catalysts, such as $\alpha,\alpha'$-azodiisobutyronitrile. The solvent or emulsifying medium for the process, the concentration of solids in the solvent or emulsifying medium and the proportions of monomers used for the various polymers are set out in the following table.

| Polymer | Preparative Method | Hydrophilic Monomer | | | Hydrophobic Monomer | | |
|---|---|---|---|---|---|---|---|
| | | Acrylic Acid | Vinyl pyrollidone | Other | Methyl Methacrylate | Methyl Acrylate | Other |
| 1 | 50% solution in ethanol | 55 | — | — | 35 | — | 10 EHA |
| 2 | 50% solution in ethanol | 40 | — | — | — | 40 | 20 EHA |
| 3 | 50% solution in ethanol | 40 | — | — | — | 60 | — |
| 4 | 50% solution in ethanol | — | — | 40 MAA | — | 60 | — |
| 5 | 50% solution in ethanol | 42 | — | — | — | 58 | — |
| 6 | 50% solution in ethanol | 20 | 30 | — | — | 50 | — |
| 7 | 50% solution in ethanol | 10 | 30 | — | — | 45 | 15 EHA |
| 8 | 50% solution in ethanol | 10 | 10 | — | — | 80 | — |
| 9 | 50% solution in ethanol | 10 | — | — | 59 | 31 | — |
| 10 | Solution in acetone | 35.6 | — | — | 64.4 | — | — |
| 11 | Solution in acetone | 25 | — | — | — | — | 75 LMA |
| 12 | Solution in acetone | — | — | 48.5 MAn | — | — | 51.5 Styrene |
| 13 | Solution in ethanol | 75 | — | — | — | — | 25 Styrene |
| 14 | Solution in ethanol | 40 | — | — | 60 | — | — |
| 15 | Solution in acetone | 22 | — | — | — | — | 78 BMA |
| 16 | Solution in ethanol | 10 | 40 | — | 50 | — | — |
| 17 | Solution in ethanol | 20 | 35 | — | 45 | — | — |

| | | Hydrophilic Monomer | | | Hydrophobic Monomer | | |
|---|---|---|---|---|---|---|---|
| Polymer | Preparative Method | Acrylic Acid | Vinyl pyrollidone | Other | Methyl Methacrylate | Methyl Acrylate | Other |
| 18 | Solution in ethanol | 21 | — | — | — | — | 79 EHA |
| 19 | Solution in ethanol | 25 | — | — | — | — | 75 LMA |
| 20 | Solution in ethanol | — | — | 40 MAA | 60 | — | — |
| 21 | Solution in ethanol | 25 | — | — | — | — | 75 Styrene |

In this Table:
MAA = Methyacrylic Acid
MAn = Maleic Anhydride
EHA = 2-Ethyl hexyl acrylate
LMA = Lauryl methacrylate
BMA = Butyl methacrylate

EXAMPLE 1

Pilocarpine base is added to the solutions of polymers 1 to 4 in an amount to give 4 to 10% pilocarpine base content calculated on total solids. In particular, when using the solution of polymer 2 the pilocarpine content was 6% based on total solids. This particular solution was cast in the form of a film having 0.3 mm thickness. Lenticular portions cut from this film were put in the eyes of rabbits, Myosis was obtained after a period of 40 hours. The polymer jellified and disappeared. No irritation or any other toxic effect was observed.

EXAMPLE 2

In the same manner as Example 1, pilocarpine salts containing 6% pilocarpine were prepared from each of polymers 5 to 9. Ocular inserts made from the salts from polymers 5, 6 and 7 dissolved in the eyes of rabbits after about 4 hours, leaving a miotic effect for 6 to 8 hours whilst ocular inserts made from polymers 8 and 9 were tested in human patients and produced a miotic effect for about 24 hours without dissolving in the eye.

EXAMPLE 3

The solution of polymer 10 was partially neutralised with pilocarpine base to give a final emulsion containing 8% base. This emulsion was used in human glaucoma patients. One drop gave good control of the intraocular pressure for period of between 8 and 20 hours, depending on the patient.

EXAMPLE 4

The solution of polymer 11 was partially neutralised with pilocarpine base to give a final pilocarpine content of 12%. One drop of this material applied to human glaucoma patients gave good control of the intra-ocular pressure for periods of between 12 and 40 hours.

EXAMPLE 5

Other eye drop emulsions were made by extracting polymer 12 or 13 from its solution, dispersing it in water and neutralising 100 gms of the polymer with 72 or 43 grams of pilocarpine base respectively, to form a stable emulsion in water.

EXAMPLE 6

Polymer 14 was precipitated from the solution in which it was made by the addition of petroleum ether and was then dissolved in an acetone solution of Lidocaine base. When complete solution of the polymer lidocaine salt had been achieved water was added dropwise with stirring. The acetone was removed under vacuum. A stable emulsion was obtained containing 10% lidocaine base in the form of the polymer salt. This emulsion was tested on the sciatic nerves of rats, using Lidocaine hydrochloride as control. The nerve was subjected to electric pulses and the twitch of distal muscles was recorded. Onset of anaesthesia using the polymer-Lidocaine emulsion and the Lidocaine hydrochloride solution was the same: 5 minutes. But maximum blockage time was 2½ hours for the hydrochloride and more than 5 hours for the polymer-Lidocaine emulsion.

In the same manner as above, an emulsion of a salt of 7% Lidocaine base with polymer 15 can be obtained.

EXAMPLE 7

An ointment was prepared by mixing 1 part of the emulsion prepared in Example 6 using the salt of polymer 14 with 1 part of a 4% solution of a hydroxyethyl cellulose supplied by Hercules Corporation under the trade mark "Natrosol" 250HRR. The resultant ointment was clear and thick and contained 5% of the base in the form of its polymer salt.

EXAMPLE 8

Polymer 16 was precipitated from its solution and dried in the same way as is described in Example 6. 80 gram of this polymer were dissolved in ehtanol and to this solution 20 gram of Lidocaine base dissolved in acetone were added. The salt obtained gave a clear solution from which a film was cast which, after drying, contained 20% Lidocaine base in the polymer salt form. In a similar manner a salt containing 20% Lidocaine base could be formed from polymer 17. The resultant dried film was brittle and could be ground to a fine powder.

EXAMPLE 9

An emulsion of polymer 15 was formed as in Example 6 containing 14% Lidocaine base. Mice were injected subcutaneously with 400 mg of Lidocaine in the form of the above polymer salt. After two hours, all the mice were still alive, whereas of the control group of mice, given the same amount of Lidocaine in the form of the hydrochloride, 80% had died.

EXAMPLE 10

Polymer 18 was precipitated from its solution by the additon of petroleum ether and dried. The purified polymer was re-dissolved in acetone, reacted with Lidocaine base and cast as a film containing 38% of the base in the form of the polymer salt. This material was used in the form of buccal strips for topical anaesthesia in the mouth. It produced two hours of full anaesthesia, plus one hour of numbness.

In generally similar manner to that given in Example 6 emulsions of Lidocaine with polymers 19, 20 and 21 can be obtained. Similarly, in any of Examples 6 to 10 Lidocaine can be replaced by any other pharmaceutically effective compound having a basic group, especially an amino group. Thus in other Examples of the invention emulsions, powders or other forms of salts are made by the methods described above except that in place of Lidocaine other local anaesthetics and analgesics are used, for example Morphine, Cocaine, Dibucaine, as well as other products such as any of those listed above as being suitable for use in the invention.

EXAMPLE 11

A solution polymer in acetone was prepared, using as monomers methyl methacrylate—72%, acrylic acid—13%, 2-ethyl hexyl acrylate—15%. The solution was mixed with Sulfadimetoxine in an amount sufficient to neutralise 50% of the acid content.

After 3 hours of mixing, a clear solution was obtained. This was cast as a film which, after drying, was shaken in Sorensen solution (0.9% sodium chloride, pH 7.2).

After one day the film released 1.3% of its sulfa content, and after five days—13.3%.

This type of material is especially useful in veterinary applications.

What we claim is:

1. A method of preparing a stable fluid composition for sustained release of a phramaceutical compound comprising the steps of:
   dissolving a pharmaceutically pure, acid group containing, water-insoluble, synthetic polymer and a salt-forming basic nitrogen containing pharmaceutically effective compound in organic solvent to form a salt of the polymer and the pharmaceutical compound in organic solution,
   slowly adding water to said salt solution without coagulating the polymer salt, and
   removing the organic solvent under vacuum to form a stable emulsion consisting of said salt in water;
   said polymer comprising from 10 to 75% by weight of at least one hydrophilic monomer and from 25 to 90% by weight of at least one hydrophobic monomer; at least 50% of the acid groups of said polymer being neutralized.

2. A stable fluid composition for sustained release of a pharmaceutical compound, said composition consisting of a stable emulsion in water of a salt of a pharmaceutically pure, acid group containing, water-insoluble synthetic polymer and a salt-forming basic nitrogen containing, pharmaceutically effective compound; said polymer comprising from 10 to 75% by weight of at least one hydrophilic monomer and from 25 to 90% by weight of at least one hydrophobic monomer; at least 50% of the acid groups of said polymer being neutralized; said emulsion being formed by dissolving purified polymer and pharmaceutical compound in an organic solvent to form the desired salt in organic solution, slowly adding water to the solution without coagulating the polymer salt and removing the organic solvent under vacuum.

3. The composition of claim 2 wherein the hydrophilic groups of the polymer are selected from acrylic acid, vinyl pyrrolidone, methacrylic acid and maleic anhydride and the hydrophobic groups of the polymer are selected from methyl methacrylate, butyl methacrylate, lauryl methacrylate, methylacrylate, 2-ethyl-hexacrylate and styrene.

4. The composition of claim 1 in which the monomers from which the polymer is made comprise at least one monomer selected from the class consisting of acrylic acid and vinyl pyrrolidone.

5. The composition of claim 4 in which the monomers include 20 to 55% acrylic acid.

6. The composition of claim 2 in which the pharmaceutically effective compound is an alkaloid.

7. The composition of claim 2 in which the pharmaceutically effective compound is pilocarpine.

8. The composition of claim 2 in which the pharmaceutically effective compound is cocaine, dibucaine or morphine.

9. The composition of claim 2 in which the pharmaceutically effective compound is a local anaesthetic.

10. The composition of claim 2 in which the pharmaceutically effective compound is an analgesic.

11. The composition of claim 10 in which the compound is lidocaine.

12. The composition of claim 2 in which the pharmaceutically effective compound is a sulphonamide.

13. The composition of claim 12 in which the compound is sulphadimetoxin.

14. The composition of claim 2 in the form of an emulsion wherein the carrier is in the form of a liquid.

15. The composition of claim 14 wherein the pharmaceutically effective compound is pilocarpine.

16. The composition as recited in claim 2 wherein the water-insoluble polymer is capable of absorbing water to form a gel.

* * * * *